(12) United States Patent
Meng et al.

(10) Patent No.: US 9,901,687 B2
(45) Date of Patent: Feb. 27, 2018

(54) IMPLANTABLE DRUG-DELIVERY DEVICES, AND APPARATUS AND METHODS FOR REFILLING THE DEVICES (71) Applicants: Ellis Fan-chuin Meng, Alhambra, CA (US); Mark S. Humayun, Glendale, CA (US); Ronalee Lo Mann, Menlo Park, CA (US); Po-Ying Li, Monrovia, CA (US); Saloomeh Saati, Placentia, CA (US)

(72) Inventors: Ellis Fan-chuin Meng, Alhambra, CA (US); Mark S. Humayun, Glendale, CA (US); Ronalee Lo Mann, Menlo Park, CA (US); Po-Ying Li, Monrovia, CA (US); Saloomeh Saati, Placentia, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 874 days.

(21) Appl. No.: 13/868,649

(22) Filed: Apr. 23, 2013

(65) Prior Publication Data
US 2013/0289482 A1 Oct. 31, 2013

Related U.S. Application Data (62) Division of application No. 12/348,178, filed on Jan. 2, 2009, now abandoned.
(Continued)

(51) Int. Cl.
*A61M 39/02* (2006.01)
*A61M 5/42* (2006.01)
(Continued)

(52) U.S. Cl.
CPC ........... *A61M 5/427* (2013.01); *A61F 9/0017* (2013.01); *A61M 5/14276* (2013.01); *A61M 5/158* (2013.01); *A61M 5/46* (2013.01); *A61M 39/0208* (2013.01); *A61M 2005/14284* (2013.01); *A61M 2039/0238* (2013.01);
(Continued)

(58) Field of Classification Search
CPC ............. A61F 9/0017; A61M 5/14276; A61M 39/0208; A61M 2209/045; A61M 2210/0612
See application file for complete search history.

(56) References Cited

U.S. PATENT DOCUMENTS 3,731,681 A 5/1973 Blackshear et al.
3,916,899 A 11/1975 Theeuwes et al.
(Continued)

FOREIGN PATENT DOCUMENTS

CA 946696 A1 5/1974
CH 570169 A5 12/1975
(Continued)

OTHER PUBLICATIONS

Mexican Patent Application No. MX/a/2010/007382, Mexican Office Action dated Sep. 30, 2013, 4 pages.
(Continued)

*Primary Examiner* — Aarti B Berdichevsky
(74) *Attorney, Agent, or Firm* — Morgan, Lewis & Bockius LLP (57) ABSTRACT In various embodiments, a needle is employed in refilling drug-delivery devices.

18 Claims, 6 Drawing Sheets

Related U.S. Application Data (60) Provisional application No. 61/018,747, filed on Jan. 3, 2008.

(51) Int. Cl.
*A61F 9/00* (2006.01)
*A61M 5/142* (2006.01)
*A61M 5/158* (2006.01)
*A61M 5/46* (2006.01)

(52) U.S. Cl.
CPC .............. *A61M 2205/3523* (2013.01); *A61M 2205/581* (2013.01); *A61M 2205/582* (2013.01); *A61M 2205/583* (2013.01); *A61M 2205/6054* (2013.01); *A61M 2205/6063* (2013.01); *A61M 2209/045* (2013.01); *A61M 2210/0612* (2013.01)

(56) References Cited

U.S. PATENT DOCUMENTS

| | | |
|---|---|---|
| 3,977,404 A | 8/1976 | Theeuwes |
| 4,150,673 A | 4/1979 | Watt |
| 4,164,560 A | 8/1979 | Folkman et al. |
| 4,543,088 A | 9/1985 | Boatman et al. |
| 4,553,973 A | 11/1985 | Edgren |
| 4,573,994 A | 3/1986 | Fischell et al. |
| 4,673,394 A * | 6/1987 | Fenton et al. ................. 604/175 |
| 4,718,894 A * | 1/1988 | Lazorthes ............ A61M 5/1428 604/185 |
| 4,738,657 A | 4/1988 | Hancock et al. |
| 4,751,926 A | 6/1988 | Sasaki |
| 4,760,837 A | 8/1988 | Petit |
| 4,781,675 A | 11/1988 | White |
| 4,781,695 A | 11/1988 | Dalton |
| 4,804,054 A | 2/1989 | Howson et al. |
| 4,838,887 A | 6/1989 | Idriss |
| 4,853,224 A | 8/1989 | Wong |
| 4,888,176 A | 12/1989 | Langer et al. |
| 4,955,861 A | 9/1990 | Enegren et al. |
| 4,959,217 A | 9/1990 | Sanders et al. |
| 5,007,647 A | 4/1991 | Gulick |
| 5,135,499 A | 8/1992 | Tafani et al. |
| 5,147,647 A | 9/1992 | Darougar et al. |
| 5,164,188 A | 11/1992 | Wong |
| 5,171,213 A | 12/1992 | Price, Jr. |
| 5,178,604 A | 1/1993 | Baerveldt et al. |
| 5,201,715 A | 4/1993 | Masters |
| 5,252,192 A | 10/1993 | Ludwig |
| 5,312,357 A | 5/1994 | Buijs et al. |
| 5,389,077 A | 2/1995 | Melinyshyn et al. |
| 5,407,441 A | 4/1995 | Greenbaum |
| 5,443,505 A | 8/1995 | Wong et al. |
| 5,462,739 A | 10/1995 | Dan et al. |
| 5,472,436 A | 12/1995 | Fremstad |
| 5,476,445 A | 12/1995 | Baerveldt et al. |
| 5,478,328 A | 12/1995 | Silverman et al. |
| 5,702,432 A * | 12/1997 | Chen ..................... A61N 5/062 604/21 |
| 5,704,520 A | 1/1998 | Gross et al. |
| 5,725,017 A | 3/1998 | Elsberry et al. |
| 5,725,493 A | 3/1998 | Avery et al. |
| 5,798,115 A | 8/1998 | Santerre et al. |
| 5,824,072 A | 10/1998 | Wong |
| 5,830,173 A | 11/1998 | Avery et al. |
| 5,836,935 A | 11/1998 | Ashton et al. |
| 5,868,697 A | 2/1999 | Richter et al. |
| 5,904,144 A | 5/1999 | Hammang et al. |
| 5,989,579 A | 11/1999 | Darougar et al. |
| 6,144,106 A | 11/2000 | Bearinger et al. |
| 6,251,090 B1 | 6/2001 | Avery et al. |
| 6,264,971 B1 | 7/2001 | Darouqar et al. |
| 6,281,192 B1 | 8/2001 | Leahy et al. |
| 6,375,972 B1 | 4/2002 | Guo et al. |
| 6,416,777 B1 | 7/2002 | Yaacobi |
| 6,478,783 B1 | 11/2002 | Moorehead |
| 6,519,569 B1 | 2/2003 | White et al. |
| 6,520,936 B1 | 2/2003 | Mann |
| 6,527,744 B1 | 3/2003 | Kriesel et al. |
| 6,537,268 B1 | 3/2003 | Gibson et al. |
| 6,564,087 B1 | 5/2003 | Pitris et al. |
| 6,669,950 B2 | 12/2003 | Yaacobi |
| 6,713,081 B2 | 3/2004 | Robinson et al. |
| 6,719,750 B2 | 4/2004 | Varner et al. |
| 6,852,106 B2 | 2/2005 | Watson et al. |
| 6,962,580 B2 | 11/2005 | Adams et al. |
| 6,976,974 B2 | 12/2005 | Houde et al. |
| 7,070,577 B1 | 7/2006 | Hailer et al. |
| 7,191,011 B2 * | 3/2007 | Cantlon ........................ 607/60 |
| 7,276,050 B2 | 10/2007 | Franklin |
| 7,497,850 B2 * | 3/2009 | Halili ................ A61M 5/14276 604/288.01 |
| 7,637,897 B2 | 12/2009 | Ginggen |
| 8,025,639 B2 | 9/2011 | Powers et al. |
| 8,177,762 B2 | 5/2012 | Beasley et al. |
| 8,202,259 B2 | 6/2012 | Evans et al. |
| 8,348,897 B2 | 1/2013 | Shih et al. |
| 9,050,407 B2 | 6/2015 | Shih et al. |
| 2002/0040208 A1 | 4/2002 | Flaherty et al. |
| 2002/0103412 A1 | 8/2002 | Trirnrner |
| 2002/0128604 A1 | 9/2002 | Nakajima |
| 2002/0188282 A1 | 12/2002 | Greenberg |
| 2003/0014036 A1 | 1/2003 | Varner et al. |
| 2003/0064088 A1 | 4/2003 | Carvalho et al. |
| 2003/0069560 A1 | 4/2003 | Adarnis et al. |
| 2003/0078195 A1 | 4/2003 | Kristensen et al. |
| 2003/0141618 A1 | 7/2003 | Braithwaite et al. |
| 2004/0028655 A1 | 2/2004 | Nelson et al. |
| 2004/0143221 A1 | 7/2004 | Shadduck |
| 2004/0199130 A1 | 10/2004 | Chornenky et al. |
| 2005/0175708 A1 | 8/2005 | Carrasquillo et al. |
| 2005/0187515 A1 | 8/2005 | Varrichio et al. |
| 2005/0208103 A1 | 9/2005 | Adarnis et al. |
| 2006/0089619 A1 | 4/2006 | Ginggen |
| 2006/0167435 A1 | 7/2006 | Adamis et al. |
| 2006/0235428 A1 | 10/2006 | Silvestrini |
| 2006/0258994 A1 | 11/2006 | Avery |
| 2006/0259015 A1 | 11/2006 | Steinbach |
| 2006/0264897 A1 | 11/2006 | Lenarz et al. |
| 2007/0021735 A1 | 1/2007 | Bhavaraju et al. |
| 2007/0078391 A1 | 4/2007 | Wortley et al. |
| 2007/0112328 A1 | 5/2007 | Steinbach et al. |
| 2007/0255235 A1 | 11/2007 | Olsen et al. |
| 2007/0255261 A1 | 11/2007 | Haase |
| 2007/0287989 A1 * | 12/2007 | Crawford .......... A61M 5/16836 604/507 |
| 2008/0039792 A1 | 2/2008 | Meng et al. |
| 2008/0045930 A1 | 2/2008 | Makin et al. |
| 2008/0181930 A1 | 7/2008 | Rodstrom et al. |
| 2008/0234637 A1 | 9/2008 | McConnell et al. |
| 2009/0028824 A1 | 1/2009 | Chiang et al. |
| 2009/0088732 A1 | 4/2009 | Villegas |
| 2009/0118683 A1 | 5/2009 | Hanson et al. |
| 2009/0192493 A1 * | 7/2009 | Meng et al. ................... 604/513 |
| 2009/0227855 A1 | 9/2009 | Hill et al. |
| 2009/0234303 A1 * | 9/2009 | Halili ................ A61M 5/14276 604/288.01 |
| 2009/0240241 A1 * | 9/2009 | Hyde et al. ................ 604/891.1 |
| 2009/0306595 A1 | 12/2009 | Shih et al. |
| 2009/0311133 A1 | 12/2009 | Pang et al. |
| 2010/0004639 A1 | 1/2010 | Pang et al. |
| 2010/0277316 A1 | 11/2010 | Schlangen et al. |
| 2012/0234433 A1 | 9/2012 | Shih et al. |
| 2013/0102962 A1 | 4/2013 | Shih et al. |
| 2013/0116664 A1 | 5/2013 | Tai et al. |
| 2013/0116665 A1 | 5/2013 | Humayun et al. |
| 2013/0116666 A1 | 5/2013 | Shih et al. |
| 2013/0226105 A1 * | 8/2013 | Hyde et al. .............. 604/288.01 |

FOREIGN PATENT DOCUMENTS

| | | |
|---|---|---|
| CN | 1321096 A | 11/2001 |
| CN | 102202706 A | 9/2011 |
| CN | 103349803 A | 10/2013 |

(56) References Cited

FOREIGN PATENT DOCUMENTS

| | | |
|---|---|---|
| CN | 103394142 A | 11/2013 |
| CN | 103608054 A | 2/2014 |
| DE | 3915708 | 2/1990 |
| DE | 3390255 C2 | 6/1992 |
| DE | 4436540 | 4/1996 |
| DE | 202004008151 | 10/2005 |
| EP | 0251680 | 1/1988 |
| EP | 0646381 | 4/1995 |
| EP | 1649884 | 4/2006 |
| EP | 2240220 A2 | 10/2010 |
| EP | 2266643 A2 | 12/2010 |
| EP | 2266643 A3 | 3/2011 |
| EP | 2320972 A2 | 5/2011 |
| EP | 2686038 A1 | 1/2014 |
| EP | 2727616 A1 | 5/2014 |
| EP | 2760504 A2 | 8/2014 |
| FR | 2091189 A5 | 1/1972 |
| GB | 1345764 | 2/1974 |
| IE | 38474 | 3/1978 |
| JP | 2-191468 A | 7/1990 |
| JP | 2002-529185 A | 9/2002 |
| JP | 3503852 B2 | 3/2004 |
| JP | 2004-535886 A | 12/2004 |
| JP | 2005-131414 A | 5/2005 |
| JP | 2005-521433 A | 7/2005 |
| JP | 2006-501014 A | 1/2006 |
| JP | 2006-526430 A | 11/2006 |
| JP | 2011-509120 A | 3/2011 |
| JP | 2014-028145 A | 2/2014 |
| WO | WO-84/001718 | 5/1984 |
| WO | WO-95/13838 | 5/1995 |
| WO | WO-99/17749 | 4/1999 |
| WO | WO-99/38552 | 8/1999 |
| WO | WO-99/62576 | 12/1999 |
| WO | WO-2000/26367 | 5/2000 |
| WO | WO-2000/40089 | 7/2000 |
| WO | 2000/074751 A1 | 12/2000 |
| WO | WO-01/12158 | 2/2001 |
| WO | 2001/056634 A1 | 8/2001 |
| WO | WO-01/66173 | 9/2001 |
| WO | WO-01/94784 | 12/2001 |
| WO | 2002/040208 A1 | 5/2002 |
| WO | WO-2003/002170 | 1/2003 |
| WO | 2003/009784 A1 | 2/2003 |
| WO | WO-03/009774 | 2/2003 |
| WO | WO-03/024360 | 3/2003 |
| WO | WO-2004/014969 | 2/2004 |
| WO | WO-2004/066871 | 8/2004 |
| WO | 2004/073765 A2 | 9/2004 |
| WO | WO-2004/073551 | 9/2004 |
| WO | WO-2005/046769 | 5/2005 |
| WO | WO-2006/012280 | 2/2006 |
| WO | WO-2006/014793 | 2/2006 |
| WO | WO-2006/075016 | 7/2006 |
| WO | 2006/096686 A1 | 9/2006 |
| WO | 2006/114638 A2 | 11/2006 |
| WO | WO-2007/084765 | 7/2007 |
| WO | WO-2007/106557 | 9/2007 |
| WO | 2009/137777 A2 | 11/2009 |
| WO | 2011/022484 A1 | 2/2011 |
| WO | 2012/125695 A1 | 9/2012 |
| WO | 2013/052414 A2 | 4/2013 |
| WO | 2013/052414 A3 | 6/2013 |

OTHER PUBLICATIONS

International Patent Application No. PCT/US2012/029029, International Search Report and Written Opinion dated Jul. 26, 2012, 13 pages.
International Patent Application No. PCT/US2012/029029, International Preliminary Report on Patentability dated Sep. 26, 2013, 9 pages.
International Patent Application No. PCT/US2012/058286, International Search Report dated Apr. 5, 2013, 5 pages.
Examination Report Received for European Patent Application No. 09701298.3, dated Jan. 29, 2013, 5 pages.
Examination Report Received for European Patent Application No. 10008072.0, dated Jun. 17, 2013, 6 pages.
Examination Report Received for Australian Patent Application No. 2012230033, dated Jul. 9, 2014, 4 pages.
Examination Report Received for European Patent Application No. 09743763.6, dated Sep. 9, 2014, 3 pages.
Extended European Search Report received for Application No. 14152346.4, dated Apr. 9, 2014, 6 pages.
Examination Report Received for Japanese Patent Application No. 2013-157652, dated Jul. 29, 2014, 3 pages. (Official Copy Only).
Examination Report Received for Japanese Patent Application No. 2013-243564, dated Sep. 18, 2014, 7 pages (4 pages of English Translation and 3 pages of Official copy).
Examination Report Received for Mexican Patent Application No. MX/a/2010/012212, dated Mar. 3, 2014.
Examination Report Received for Mexican Patent Application No. MX/a/2010/012212, dated Jun. 5, 2014, 1 page. (Official Copy Only).
Examination Report Received for Mexican Patent Application No. MX/a/2010/007382, dated May 30, 2014.
PCT International Patent Application No. PCT/US2012/58286, International Preliminary Report on Patentability dated Apr. 10, 2014, 10 pages.
"FDA Approves an Industry First!—The MED-EL Cochlear Implant System is FDA Approved for Use With Magnetic Resonance Imaging (MRI)," PR Newswire, Durham, N.C., Jun. 18, 2003, 3 pages.
"Krupin Eye Valve with Scleral Buckle, Krupin Eye Valve With Disk," Hood Laboratories Catalogue, F 079 Rev. Nov. 1992, 4 pages.
"The Optimed Advantage—Glaucoma Pressure Regulator," Optimed Advertising Brochure, Journal of Glaucoma, vol. 2, No. 3, 1993, 4 pages.
Chen et al. "Floating-Disk Parylene Micro Check Valve," Micro Electro Mechanical Systems, 2007, IEEE 20th International Conference on MEMS, Jan. 21-25, 2007, 4 pages.
Chen et al. "Floating-Disk Parylene Microvalve for Self-Regulating Biomedical Flow Controls," IEEE 21st International Conference on MEMS, 2008, Jan. 13-17, 2008, 4 pages.
Chen et al. "Surface-Micromachined Parylene Dual Valves for On-Chip Unpowered Microflow Regulation," Journal of Microelectromechanical Systems, vol. 16, No. 2, Apr. 2007, pp. 223-231.
Choudhri et al. "A Comparison of Dorzolamide-Timolol Combination Versus the Concomitant Drugs," American Journal of Ophthalmology, Dec. 2000, 130, pp. 832-833.
Eliason et al. "An Ocular Perfusion System," Invest. Ophthalmol. Vis. Sci., vol. 19, No. 1, Jan. 1980, pp. 102-105.
Hashizoe et al. "Scleral Plug of Biodegradable Polymers for Controlled Release in the Vitreous" Arch Ophthalmol, vol. 112, Oct. 1994, pp. 1380-1384.
Jabs "Treatment of Cytomegalovirus Retinitis—1992," Arch Ophthlmol, vol. 110, Feb. 1992, pp. 185-187.
Khouri et al. "Use of Fixed-Dose Combination Drugs for the Treatment of Glaucoma," Drugs Aging, 2007,24, 12, pp. 1007-1016.
Kimura et al. "A New Vitreal Drug Delivery System Using an Implantable Biodegradable Polymeric Device," Investigative Ophthalmology & Visual Science, May 1994, vol. 35, No. 6; pp. 2815-2819.
Lo et al. "A Refillable Polymer Drug Delivery Device for Treatment of Ocular Diseases," The Royal Society of Chemistry, Jan. 1, 2007, 28 pages.
Michelson et al. "Experimental Endophtalmitis Treated With an Implantable Osmotic Minipump," Arch Ophthalmol, vol. 97, Jul. 1979, pp. 1345-1346.
Miki, et al. "A Method for Chronic Drug Infusion Into the Eye," Japanese Journal of Ophthalmology, vol. 28, 1984, pp. 140-146.
Pincus et al. "Why are Only 50% of Courses of Anti-Tumor Necrosis Factor Agents Continued for Only 2 Years in Some (56) References Cited

OTHER PUBLICATIONS

Settings? Need for Longterm Observations in Standard Care to Compliment Clinical Trials," Journal of Rheumatology, 2006, 33, 12, pp. 2372-2375.

Pope et al. "MRI in Patients with High-Grade Gliomas Treated with Bevacizumab and Chemotherapy," Neurology, 2006,66, pp. 1258-1260.

Rubsamen et al. "Prevention of Experimental Proliferative Vitreoretinopathy With a Biodegradable Intravitreal Implant for the Sustained Release of Fluorouracil," Arch Ophthalmol, vol. 112, Mar. 1994, pp. 407-413.

Sanborn et al. "Sustained-Release Ganciclovir Therapy for Treatment of Cytomegalovirus Retinitis," Arch Ophthmol, vol. 110, Feb. 1992; pp. 188-195.

Smith et al. "Intravitreal Sustained-Release Ganiclovir," Arch Ophthlmol, vol. 110, Feb. 1992, pp. 255-258.

Stark-Vance, "Bevacizumab and CPT-11 in the Treatment of Relapsed Malignant Glioma,".

Steyer "Alcon Eye-Drug Setback Raises the Stakes," The Street. Com, Oct. 14, 2004, 4 pages.

Strohmaier et al. "The Efficacy and Safety of the Dorzolamide-Timolol Combination Versus the Concomitant Administration of its Components," Ophthalmology, Oct. 1998, vol. 105, No. 10, pp. 1936-1944.

Xie et al. "An Electrochemical Pumping System for On-Chip Gradient Generation," Analytical Chemistry, 8 pages (A-H).

Examination Report for European Patent Application No. 07753177.0, dated Jan. 29, 2009, 6 pages.

Invitation to Pay Additional Fees and Partial International Search for PCT Application No. PCT/US2007/006530, dated Jul. 31, 2007, 7 pages.

International Search Report for PCT Application No. PCT/US2007/006530, dated Nov. 12, 2007, 7 pages.

Written Opinion for PCT Application No. PCT/US2007/006530, dated Nov. 12, 2007, 10 pages.

Invitation to Pay Additional Fees and Partial International Search for PCT Application No. PCT/US2009/030019, dated Jun. 5, 2009, 5 pages.

International Search Report for PCT Application No. PCT/US2009/030019, dated Jul. 20, 2009, 7 pages.

Written Opinion for PCT Application No. PCT/US2009/030019, dated Jul. 20, 2009, 9 pages.

Invitation to Pay Additional Fees and Partial International Search for PCT Application No. PCT/US2008/087690, dated May 15, 2009, 5 pages.

International Search Report for PCT Application No. PCT/US2008/087690, dated Aug. 11, 2009, 7 pages.

Written Opinion for PCT Application No. PCT/US2008/087690, dated Aug. 11, 2009, 10 pages.

Invitation to Pay Additional Fees and Partial International Search for PCT Application No. PCT/US2009/043317, dated Nov. 16, 2009, 5 pages.

Invitation to Pay Additional Fees and Partial International Search for PCT Application No. PCT/US2009/043313, dated Nov. 16, 2009, 6 pages.

International Search Report for PCT Application No. PCT/US2009/043325, dated Dec. 11, 2009, 9 pages.

Written Opinion for PCT Application No. PCT/US2009/043325, dated Dec. 11, 2009, 9 pages.

Examination Report for European Patent Application No. 07753177.0, dated Feb. 5, 2010, 3 pages.

International Search Report for PCT Application No. PCT/US2009/043317, dated Feb. 16, 2010, 7 pages.

Written Opinion for PCT Application No. PCT/US2009/043317, dated Feb. 16, 2010, 8 pages.

International Search Report for PCT Application No. PCT/US2009/043313, dated Feb. 25, 2010, 8 pages.

Written Opinion for PCT Application No. PCT/US2009/043313, dated Feb. 25, 2010, 8 Pages.

European Search Report dated Mar. 1, 2011 for European Application No. 09701298.3 (11 pages).

Office Action dated Jan. 29, 2013 for European Patent Application No. 09701298.3 (5 pages).

Examination Report Received for European Patent Application No. 09743763.6 dated Feb. 6, 2015, 4 pages.

Examination Report Received for Chinese Patent Application No. 201310157066.7 dated Oct. 29, 2014, 10 pages (4 pages of English Translation & 6 pages of Official copy).

Examination Report Received for Chinese Patent Application No. 201280013608.7 dated Dec. 17, 2014, 16 pages (8 pages of English Translation & 8 pages of Official copy).

* cited by examiner

IMPLANTABLE DRUG-DELIVERY DEVICES, AND APPARATUS AND METHODS FOR REFILLING THE DEVICES

CROSS-REFERENCE TO RELATED APPLICATIONS

This application is a divisional of U.S. patent application Ser. No. 12/348,178, filed on Jan. 2, 2009, which claims priority to and the benefits of U.S. Provisional Patent Application No. 61/018,747 filed on Jan. 3, 2008, the entire disclosures of each of which are hereby incorporated by reference in their entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant Nos. ERC EEC-0310723 and EEC-0547544 awarded by the National Science Foundation.

TECHNICAL FIELD

In various embodiments, the invention relates to implantable drug-delivery devices and to apparatus and methods for refilling such devices.

BACKGROUND

Medical treatment often requires the administration of a therapeutic agent (e.g., medicament, drugs, etc.) to a particular part of a patient's body. Some maladies, however, are difficult to treat with currently available therapies and/or require administration of drugs to anatomical regions to which access is difficult to achieve.

A patient's eye is a prime example of a difficult-to-reach anatomical region, and many vision-threatening diseases, including retinitis pigmentosa, age-related macular degeneration (AMD), diabetic retinopathy, and glaucoma, are difficult to treat with many of the currently available therapies. For example, oral medications can have systemic side effects; topical applications may sting and engender poor patient compliance; injections generally require a medical visit, can be painful, and risk infection; and sustained-release implants must typically be removed after their supply is exhausted.

Another example is cancer, such as breast cancer or meningiomas, where large doses of highly toxic chemotherapies, such as rapamycin, bevacizumab (e.g., Avastin®), or irinotecan (CPT-11), are typically administered to the patient intravenously, which may result in numerous undesired side effects outside the targeted area.

Implantable drug-delivery devices, which may have a refillable drug reservoir, cannula, and check valve, etc., generally allow for controlled delivery of pharmaceutical solutions to a specified target. As drug within the drug reservoir depletes, the physician can refill the reservoir with, for example, a syringe, while leaving the device implanted within the patient's body.

If, however, the syringe needle is inadvertently inserted too far into the device during the refilling, the device can be damaged. Such damage may necessitate removal of the device and its replacement with another, thereby obviating some of the advantage of using the device. Even if the device is not damaged, insertion of the needle too far into the device can, for example, embed the needle tip in the bottom wall of the device's reservoir, thereby clogging the needle's lumen. Additionally, the improper insertion of the needle into the device may lead to the delivery of the drug into an improper location.

A need exists, therefore, for improved implantable drug-delivery devices, and apparatus and methods for refilling such devices.

SUMMARY OF THE INVENTION

In various embodiments, the present invention features apparatus and methods for refilling, in situ, a drug-delivery device implanted within a patient's body. The apparatus generally contain features, and the methods typically contain steps, that allow the refilling to occur in a manner that minimizes the risk of damage to the device, and thereby maximizes its effective lifetime. For example, embodiments of a refilling needle described herein employ a needle depth gauge to limit the degree to which the needle penetrates the drug-delivery device during a refilling procedure. As another example, the drug-delivery device itself may include a stop to limit the extent of the needle's penetration therein. Moreover, to aid a physician in locating a needle entry port of the drug-delivery device, and to protect the patient from inadvertent punctures by the needle, embodiments of the invention employ a visualization ring that identifies the needle entry port. These features, together with others, facilitate the rapid refilling of the drug-delivery device, while minimizing the risk of damage to the device and injury to the patient. Thus, the time spent by a physician in refilling the drug-delivery device is reduced (which may generate a cost savings), the useful life of the drug-delivery device may be lengthened, and the need to replace drug-delivery devices damaged during the course of attempts to refill them is reduced.

In general, in one aspect, embodiments of the invention feature a needle for refilling an implantable drug-delivery device. The drug-delivery device may have a needle entry port that includes a throat for receiving the needle therethrough. For its part, the needle may include a hollow shaft that terminates in a tip, a fluid exit port along the shaft proximate to the tip, and means for limiting the extent of entry of the needle into the entry port. In one embodiment, the needle tip is conically-shaped. The fluid exit port of the needle may be positioned intermediate to the tip and the limitation means.

In various embodiments, the limitation means includes a stop on the needle shaft. For example, the stop may be a ring surrounding and fixedly mounted to the shaft. The ring may have an outer diameter exceeding a width of the entry port's throat. Alternatively, the stop may be spherically-shaped, cylindrically-shaped, rectangularly-shaped, or pyramidally-shaped. In certain embodiments, the limitation means is constructed of a metal, a plastic, and/or a composite material. The limitation means may be, for example, constructed of a biocompatible material, such as polydimethylsiloxane (PDMS). (Although the ensuing discussion refers primarily to PDMS, this is for convenience, and references to PDMS are intended to connote any suitably biocompatible form of polydiorganosiloxane (i.e., silicone) polymer.) Other exemplary materials from which the limitation means may be constructed include polyimide, polypropylene, polyetheretherketone (PEEK), polycarbonate, an acetyl film, polyoxymethylene plastic, gold, stainless steel, nickel, chrome, and combinations thereof.

In general, in another aspect, embodiments of the invention feature an implantable drug-delivery device. The drug-delivery device includes a drug reservoir, a needle entry port, and a vestibule. The needle entry port may include a throat for receiving a refill needle therethrough. The throat may open into the vestibule, which may (i) be wider than the throat, (ii) include a stop on a wall opposite the throat for halting progress of a needle into the vestibule through the throat, and (iii) be in fluid communication with the drug reservoir.

In various embodiments, the drug-delivery device also includes a check valve that is located between the vestibule and the drug reservoir. For its part, the needle entry port may also include a self-sealing material (e.g., at its top surface). In one embodiment, the stop within the vestibule is sized so as to halt the progress of a needle that includes an exit port at a point at which the exit port is in fluid communication with the vestibule. A top surface of the stop may be cup-shaped. In certain embodiments, the stop is constructed of a metal, a plastic, and/or a composite material. The stop may be, for example, constructed of a biocompatible material, such as PDMS. Other exemplary materials from which the stop may be constructed include polyimide, polypropylene, PEEK, polycarbonate, an acetyl film, polyoxymethylene plastic, gold, stainless steel, nickel, chrome, and combinations thereof.

In general, in yet another aspect, embodiments of the invention feature an implantable drug-delivery device that includes a drug reservoir, a needle entry port, and a visualization ring surrounding the needle entry port. The needle entry port may include a throat for receiving a refill needle therethrough. The throat may open into a vestibule that is in fluid communication with the drug reservoir. For its part, the visualization ring may be visible through ocular tissue (e.g., a patient's conjunctiva) so as to visually indicate the position of the needle entry port.

In various embodiments, the visualization ring is constructed of a material that is biocompatible and/or withstands penetration by the refill needle. The visualization ring may include one or more fluorescent pigments, such as a luminescent aerogel, a nanoparticle, a phthalocyanine (PC) pigment, fluorescein isothiocyanate, rhodamine, coumarin, cyanine, an Alexa Fluor, a DyLight Fluor, a quantum dot, a green fluorescent protein, and/or a luciferin. In another embodiment, the visualization ring includes a light emitting diode. Alternatively, a light emitting diode present in the drug-delivery device may be located away from the visualization ring and optical fiber may be used to conduct light from the light emitting diode to and around the visualization ring. The visualization ring may also include a material that enhances surface echogenicity and acoustic shadowing. Electronics may also be present in the drug-delivery device in order to move or vibrate the visualization ring. In yet another embodiment, the visualization ring includes a magnetic material.

In general, in still another aspect, embodiments of the invention feature a method for refilling a drug-delivery device implanted within a patient. The method includes inserting, into a needle entry port of the drug-delivery device, a distal tip of a needle that includes a hollow shaft and a stop on the shaft. The needle may then be advanced into the needle entry port until the stop limits further entry of the needle into the entry port. Drug may be delivered through the hollow shaft of the needle, out a fluid exit port positioned along the shaft of the needle proximate the tip, and into the drug-delivery device. In accordance with this method, the stop may be a ring that surrounds the shaft of the needle and that has an outer diameter exceeding a width of the entry port.

In general, in a further aspect, embodiments of the invention feature another method for refilling a drug-delivery device implanted within a patient. The method includes inserting, into a needle entry port of the drug-delivery device, a distal tip of a needle. The needle may then be advanced through the needle entry port into a vestibule of the drug-delivery device until a stop positioned on a wall of the vestibule opposite the needle entry port halts further entry of the needle. Drug may be delivered through a hollow shaft of the needle, out a fluid exit port positioned along the shaft of the needle proximate the tip, and into the vestibule. The stop may halt further entry of the needle at a point at which the exit port of the needle is in fluid communication with the vestibule.

In various embodiments, these methods include locating, prior to inserting the distal tip of the needle into the needle entry port, a visualization ring that visually indicates the position of the needle entry port. The visualization ring may surround the needle entry port and be visible through the patient's conjunctiva.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

In general, embodiments of the present invention pertain to drug-delivery devices implantable within a patient's body, such as, for example, within the patient's eye, and to apparatus and methods for refilling those devices. In certain embodiments, an implantable drug-delivery device combines small size and a refillable reservoir. The small size minimizes discomfort from the device to the patient, while the refillable reservoir allows the device to be refilled in situ, rather than being replaced. As such, a fluid, such as a solution of a drug, can be supplied to the patient over extended periods of time.

Figure 1:
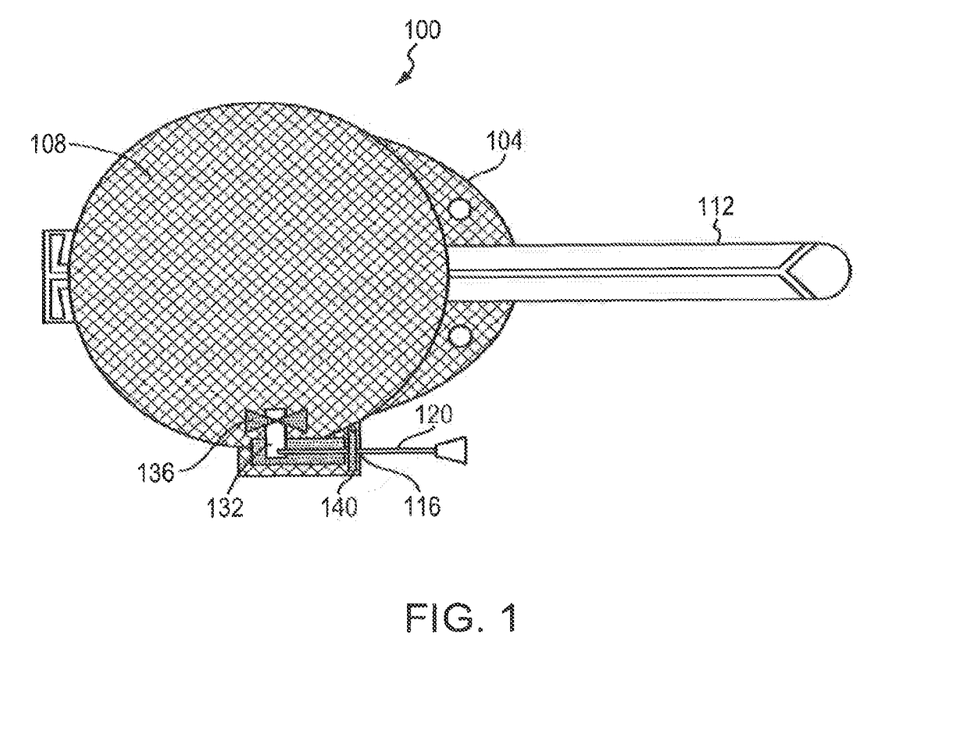
FIG. 1 illustrates a plan view of an implantable drug-delivery device in accordance with one embodiment of the invention.

FIG. 1 schematically illustrates an exemplary implantable drug-delivery device 100. The exemplary device 100 includes a base 104, a refillable drug reservoir 108, a drug-delivery cannula 112 in fluid communication with the refillable drug-reservoir 108, and a needle entry port 116 in fluid communication with the refillable drug reservoir 108 as further described below. In general, the refillable drug reservoir 108 holds the therapeutic fluid to be delivered, while the cannula 112 directs the fluid to the targeted site. The cannula 112 may be tapered to facilitate its insertion into, for example, a patient's eye. In general, the drug reservoir 108 can be refilled by inserting a refill needle 120 into and through the needle entry port 116. As described, for example, in U.S. Patent Application Publication No. 2008/0039792 entitled "MEMS Device and Method for Delivery of Therapeutic Agents," the disclosure of which is hereby incorporated herein by reference in its entirety, the drug-delivery device 100 may be mechanically (e.g., manually) or electrolytically actuated to deliver the therapeutic fluid to a targeted site.

Figure 2:
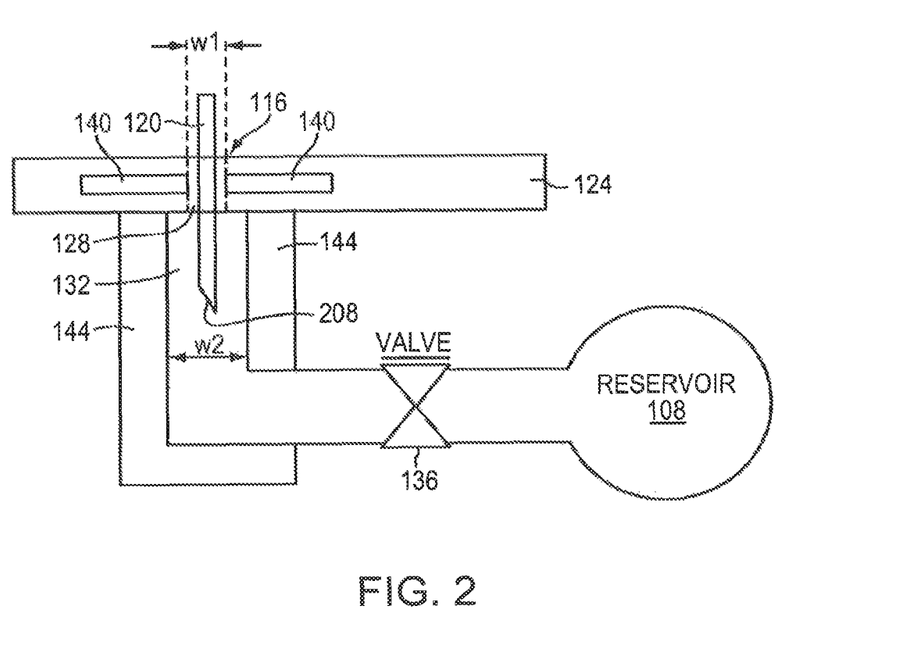
FIG. 2 schematically illustrates the internal structure between a needle entry port and a drug reservoir in accordance with one embodiment of the invention.

FIG. 2 schematically illustrates the internal structure of the drug-delivery device 100 between the needle entry port 116 and the drug reservoir 108 in accordance with one embodiment of the invention. As illustrated, the needle entry port 116 includes a surface 124 and a throat 128 for receiving the refill needle 120 therethrough. The throat 128 opens into a vestibule 132 that is in fluid communication (through, for example, a check valve 136) with the drug reservoir 108. The refill needle 120 pierces, as depicted, the surface 124 of the needle entry port 116, travels through its throat 128, and thereby gains access to the vestibule 132. In one embodiment, injection of a therapeutic fluid from the needle 120 into the vestibule 132 forces the fluid through the check valve 136 and into the reservoir 108, thereby refilling the reservoir 108.

As also illustrated in FIGS. 1 and 2, a visualization ring 140 may surround the needle entry port 116 of the implantable drug-delivery device 100. In one embodiment, the visualization ring 140 is made of a material or pigment that is visible through ocular tissue (e.g., through a patient's conjunctiva) so as to visually indicate a position of the needle entry port 116 to a user of the device 100 (e.g., a physician) when the device 100 is implanted within a patient's eye. In addition, the material or pigment forming the visualization ring 140 may be biocompatible and/or able to withstand penetration by the refill needle 120 if and when the refill needle 120 is accidently placed in contact therewith. Exemplary materials from which the visualization ring 140 may be constructed include, but are not limited to, PDMS, polyimide, PEEK, gold, stainless steel, and titanium. The material or pigment forming the visualization ring 140 may optionally fluoresce when exposed to a particular type of light, such as ultraviolet (UV) light. In daylight, fluorescent pigments have a white or light color and are therefore generally cosmetically invisible. Under excitation by UV radiation, however, the fluorescent pigments typically irradiate an intensive fluorescent color. Exemplary pigments that may form the visualization ring 140, or a portion thereof, include, but are not limited to, luminescent aerogels, nanoparticles (e.g., silicon nanoparticles), phthalocyanine (PC) pigments, fluorescein isothiocyanate, rhodamine (TRITC), coumarin, cyanine, Alexa Fluors, DyLight Fluors, quantum dots, green fluorescent proteins, and/or luciferins. By using such pigments, the visualization ring 140 and its substrates may generally be cosmetically invisible until such time as the physician exposes the ring 140 to UV light. At that point, the physician can easily visualize the ring 140, either visually or with the aid of, for example, a fluorescence stereo microscope.

The visualization ring 140 may also be made with materials that enhance surface echogenicity and acoustic shadowing so that the physician may better visualize the needle entry port 116 when using certain imaging devices. Such materials include metals, semiconductors, and advanced composite materials that cause the visualization ring 140 to become more reflective or absorbent to ultrasound waves or infrared light (in contrast to the other materials on the non-ring portions of the drug-delivery device 100 that are not desired to be visualized) during such times as when the physician uses an ultrasound scanner, an optical coherence tomography (OCT) visualization tool, or other coherence scanner for visualizing the ring 140 subcutaneously. For example, if the outer shell of the drug-delivery device 100 is made of polyimide (a less reflective material), but the visualization ring 140 is lined with gold (a more reflective material), then the visualization ring 140 will be more easily visualized by the physician when using an OCT scanner or ultrasound scanner since the light, laser, or sound will be reflected differently by the gold.

In another embodiment, the visualization ring 140 includes one or more light emitting diodes (LEDs) that illuminate during the desired time of refilling. For example, the drug-delivery device 100 may include an internal power supply (e.g., a battery) and other electronics to supply power to the LEDs. Then, the physician may activate the power supply and electronics wirelessly (e.g., using a device that emits a radio-frequency (RF) signal) to turn the LEDs on just prior to refilling the drug-delivery device 100. Alternatively, where it is desired to hermetically package the electronic devices (including the LEDs) within the drug-delivery device 100, the LEDs may be located in a different part of the drug-delivery device 100 (e.g., distant from the visualization ring 140) and a conduit, such as a bundle of optical fiber, may be used to conduct the light from the LEDs to the visualization ring 140 and also around the visualization ring 140.

In yet another embodiment, the visualization ring 140 and/or the needle entry port 116 moves up and down, or vibrates, in a manner that gives the physician a tactile sensation confirming the location of the visualization ring 140 and/or needle entry port 116. Again, such movement and/or vibration may be imparted to the visualization ring 140 and/or the needle entry port 116 through the use of electronics internal to the drug-delivery device 100. Those electronics may be activated remotely through, for example, a handheld device emitting an RF signal.

In still another embodiment, the visualization ring 140 includes a magnetic material. For example, the visualization ring 140 may be made, at least in part, from a ferromagnetic material alone, or it may include a ferromagnetic material encased in a ceramic. The refill needle 120 used in combination with such a visualization ring 140 may likewise contain magnetic materials, for example on a tip 208 and/or shaft 212 thereof, and/or on a stop 224 connected thereto (see FIG. 3). In this way, the magnetic materials of the visualization ring 140 may attract the magnetic materials of the refill needle 120, thereby aiding the physician in locating the needle entry port 116. In addition, the magnetic materials of the visualization ring 140 and the refill needle 120 may aid in aligning the shaft 212 of the refill needle 120 with the elongate axes of the throat 128 and vestibule 132, thereby preventing the needle 120 from contacting (and potentially puncturing) a sidewall 144 of the vestibule 132.

Since the needle entry port 116 may be very small, and the physician may be injecting drugs in an invasive manner, it is often useful to add a secondary or tertiary confirmatory signal for the location of the visualization ring 140 and the needle entry port 116, such as sight, sound, tactile sensation, and/or magnetic interaction.

In one embodiment, as illustrated in FIG. 2, the visualization ring 140 is embedded into (and thus completely surrounded by) the material forming the surface 124 of the needle entry port 116. In this way, the visualization ring 140 does not come into contact with the patient's body or with any medications delivered to the device 100 by the refill needle 120. In certain embodiments, this is important. For example, the use of some materials in the visualization ring 140, such as rhodamine pigments, can be toxic to the patient's body or degrade over time if not properly sealed with the material forming the surface 124.

The visualization ring 140 may be an annulus and, as illustrated in FIG. 2, its inner diameter may define the width w1 of the throat 128 through which the refill needle 120 passes when it is inserted into the needle entry port 116. Moreover, in one embodiment, the width w2 of the vestibule 132 is greater than the width w1 of the throat 128. In this way, the smaller width w1 of the throat 128 constrains the movement of the refill needle 120 as it is advanced into the vestibule 132 and aids in preventing the needle 120 from contacting (and potentially puncturing) the sidewall 144 of the vestibule 132.

In addition to the visualization ring 140, an insertion guider (not shown) may be positioned at a top surface of, or within, the needle entry port 116 to aid in guiding the refill needle 120 along the elongate axis of the vestibule 132 (and not into the sidewall 144). The insertion guider may be cylindrical in shape, or have another shape. In addition, the insertion guider may be removable and may be placed on top of the needle entry port 116 and mechanically or magnetically locked to the needle entry port 116 just prior to the refilling procedure.

As mentioned, a physician may pierce the surface 124 of the needle entry port 116 with the refill needle 120 as he or she advances the needle 120 into the vestibule 132 of the drug-delivery device 100. In one embodiment, the material of the surface 124 is self-sealing. More specifically, the surface 124 may be formed from a soft plastic material that can be punctured with the needle 120 and that reseals itself upon removal of the needle 120. In one embodiment, the self-sealing material is able to withstand multiple punctures by the needle 120, and is biocompatible. Examples of materials that may be employed for the self-sealing material include, but are not limited to, PDMS, parylene C, parylene HT, polycarbonates, polyolefins, polyurethanes, copolymers of acrylonitrile, copolymers of polyvinyl chloride, polyamides, polysulphones, polystyrenes, polyvinyl fluorides, polyvinyl alcohols, polyvinyl esters, polyvinyl butyrate, polyvinyl acetate, polyvinylidene chlorides, polyvinylidene fluorides, polyimides, polyisoprene, polyisobutylene, polybutadiene, polyethylene, polyethers, polytetrafluoroethylene, polychloroethers, polymethylmethacrylate, polybutylmethacrylate, polyvinyl acetate, nylons, cellulose, gelatin, silicone rubbers and porous rubbers. Where the self-sealing material includes a plastic that is capable of leaching or absorbing drugs that come into contact with it (e.g., silicone), parylene may be coated over the plastic so that less drug is exposed to the plastic.

Figure 3:
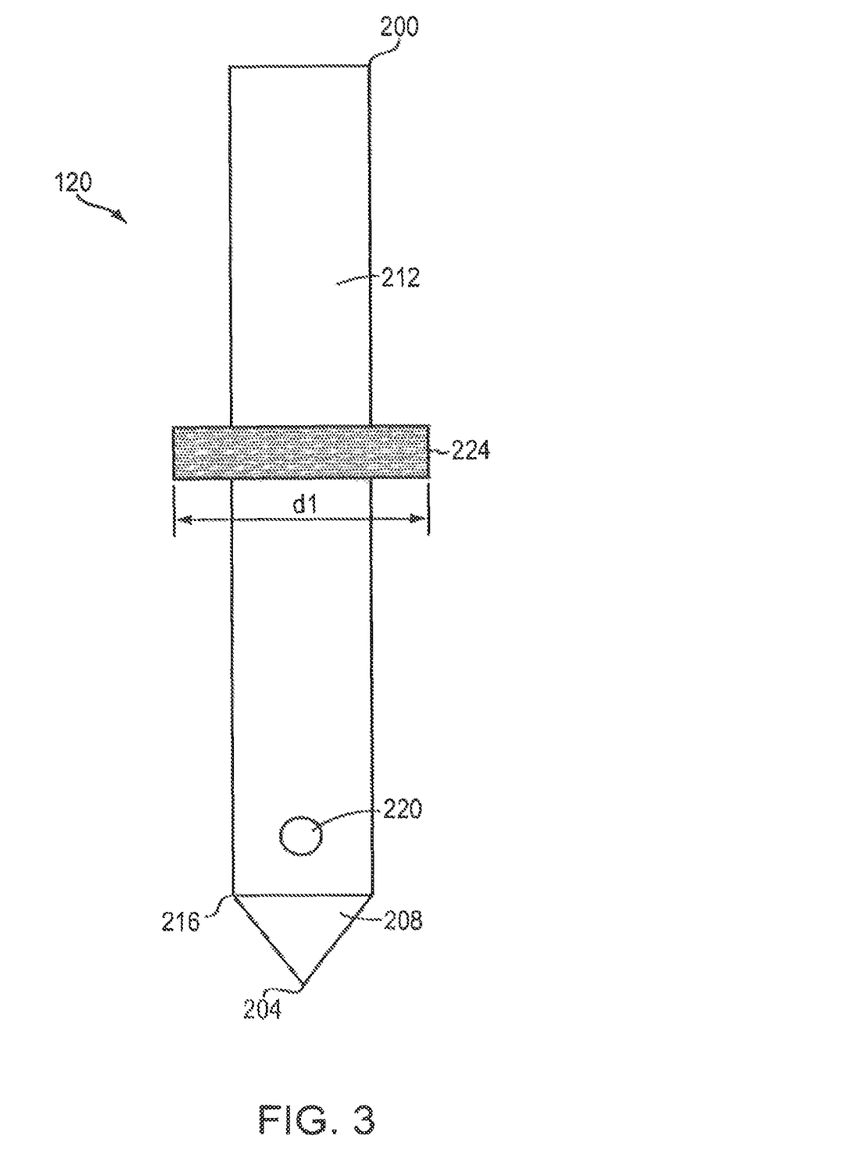
FIG. 3 is an elevation view of a refill needle in accordance with one embodiment of the invention.

FIG. 3 depicts one embodiment of the refill needle 120. As illustrated, the refill needle 120 includes a proximal end 200 (i.e., an end closest to an operator of the refill needle 120) and an opposite, distal end 204. In one embodiment, the distal end 204 of the needle 120 terminates in a tip 208, such as a conically-shaped tip. The tip 208 may, of course, have another shape suitable for piercing the surface 124 of the needle entry port 116. For example, as illustrated in FIG. 2, the distal end 204 of the refill needle 120 may be cut (or otherwise formed) at an oblique angle to form an oblique tip 208.

A hollow shaft 212 (i.e., a shaft having a lumen that extends therethrough) extends from the proximal end 200 of the refill needle 120 to a proximal end 216 of the tip 208. In addition, as illustrated, the refill needle 120 may include at least one fluid exit port 220 positioned along the shaft 212 (e.g., near the tip 208). For example, the refill needle 120 may include, near the proximal end 216 of the tip 208, two fluid exit ports 220 positioned approximately 180° apart around the circumference of the shaft 212. Alternatively, the fluid exit port(s) 220 may be positioned elsewhere along the shaft 212. The fluid exit port(s) 220 is/are in fluid communication with the lumen of the hollow shaft 212. In this way, when the refill needle 120 is positioned within the vestibule 132 of the device 100, as further described below, therapeutic fluid may be passed through the hollow shaft 212 of the needle 120, out its fluid exit port(s) 220, and into the vestibule 132. In addition, the fluid exit port(s) 220 are generally oriented transverse to the long axis of the refill needle 120. In this fashion, the refill needle 120 may be inserted into the needle entry port 116 of the device 100 with reduced risk of occluding the exit port(s) 220 with material cored from the walls of the throat 128.

Figure 4:
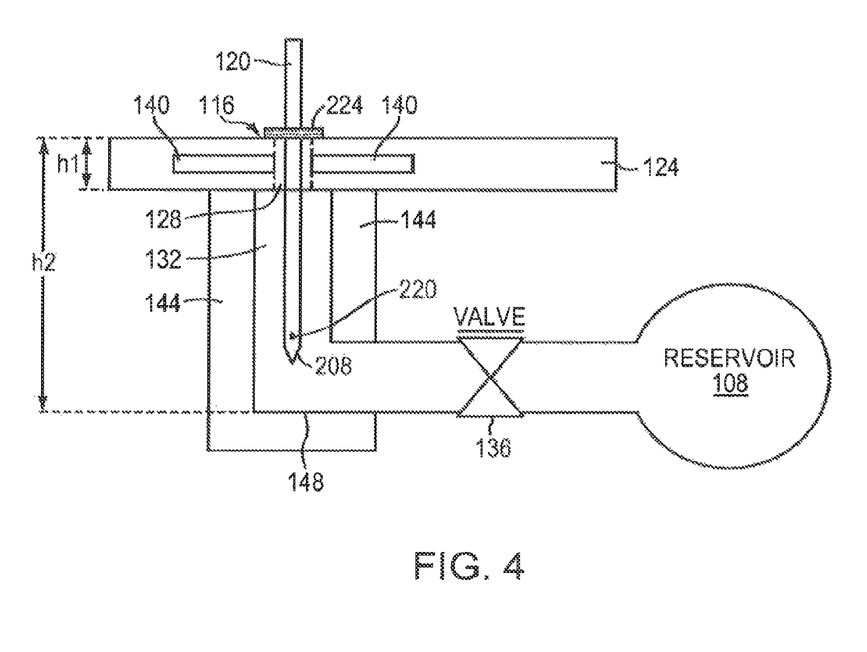
FIG. 4 schematically illustrates a refill needle, having a stop fixedly mounted thereto, inserted within a portion of a drug-delivery device in accordance with one embodiment of the invention.

With reference still to FIG. 3, the refill needle 120 may also include a means for limiting an extent of entry of the needle 120 into the needle entry port 116. For example, the limitation means may be a stop 224 fixedly mounted to the needle shaft 212. As illustrated, the stop 224 may be mounted to the shaft 212 at a point proximal to the fluid exit port(s) 220, such that the fluid exit port(s) 220 is/are positioned intermediate to the needle tip 208 and the stop 224. As illustrated in FIG. 4, by positioning the stop 224 an appropriate distance away from both the fluid exit port(s) 220 and the distal end 204 of the refill needle 120, the fluid exit port(s) 220 will be correctly positioned within the vestibule 132 of the device 100 when the stop 224 abuts the surface 124 of the needle entry port 116, and the tip 208 at the distal end 204 of the needle 120 will not contact (or pierce) the bottom wall 148 of the vestibule 132. In one embodiment, to achieve this desired effect, the stop 224 is positioned at a distance from the fluid exit port(s) 120 that is greater than the height h1 of the throat 128 of the needle entry port 116, and also at a distance from the distal end 204 of the refill needle 120 that is less than the combined height h2 of the throat 128 and vestibule 132. In this way, the stop 224 decreases the likelihood of the refill needle 220 penetrating the entire drug-delivery device 100 and entering, for example, the patient's eye. The stop 224 also prevents the tip 208 of the refill needle 120 from becoming embedded in the bottom wall 148 of the vestibule 132, where the fluid exit port(s) 220 and lumen of the needle 120 may be occluded, thereby preventing therapeutic fluid from being dispensed into the vestibule 132.

In one embodiment, as illustrated in FIG. 3, the stop 224 is a ring that surrounds the shaft 212 of the refill needle 120. So that the stop 224 halts the progress of the refill needle 120 into the vestibule 132 of the device 100 (i.e., limits the depth to which the refill needle 120 can be inserted into the vestibule 132), the ring, in one embodiment, has an outer diameter d1 that exceeds the width w1 of the throat 128. In this way, the stop 224 and the portion of the refill needle 120 proximate to the stop 224 are prevented from entering the needle entry port 116. The outer contour of the stop 224 need not take the form of a ring. For example, the stop 224 may have an outer shape that is generally spherical, cylindrical, rectangular, or pyramidal, or may be shaped in another manner suitable for carrying out the functions of the stop 224 described herein.

The stop 224 may be constructed of a metal, a plastic, a composite material, or a combination thereof. The metal, plastic, and/or composite material may be biocompatible, or not. In one embodiment, the stop 224 is constructed of PDMS. Alternatively, the stop 224 may be constructed of other material, or combinations of materials, that have the requisite mechanical strength to perform the function of the stop 224 described herein. For example, the stop 224 may also be constructed of polyimide, polypropylene, PEEK, polycarbonate, acetyl film (e.g., acetyl copolymer), polyoxymethylene plastic (e.g., Delrin®), gold, stainless steel, nickel, and/or chrome. The stop 224 may also take the form of an integral, disk-like protrusion from (and extending around) the needle shaft 212, introduced during the manufacture thereof.

In practice, an exemplary refill needle 120 may be prepared by pinching closed a hollow 30-gauge needle and deburring the closure to leave a conical tip 208 of approximately 254 µm in height. Two exit ports 220, each measuring approximately 101 µm in diameter, may then drilled through refill needle 120 approximately 127 µm above the proximal end 216 of the conical tip 208. A stop 224 may then be fabricated by laser-cutting a thin PDMS membrane into an appropriately sized ring shape. As will be understood by one of ordinary skill in the art, the inner diameter of the ring-shaped stop 224 is determined by the size of the outer diameter of the refill needle 120 (i.e., approximately 305 µm for a 30-gauge needle). The PDMS ring-shaped stop 224 may then be fitted onto the shaft 212 of the needle 120 and secured by, for example, a glue. The location on the shaft 212 to which the ring-shaped stop 224 is secured is chosen as described above.

Figure 5:
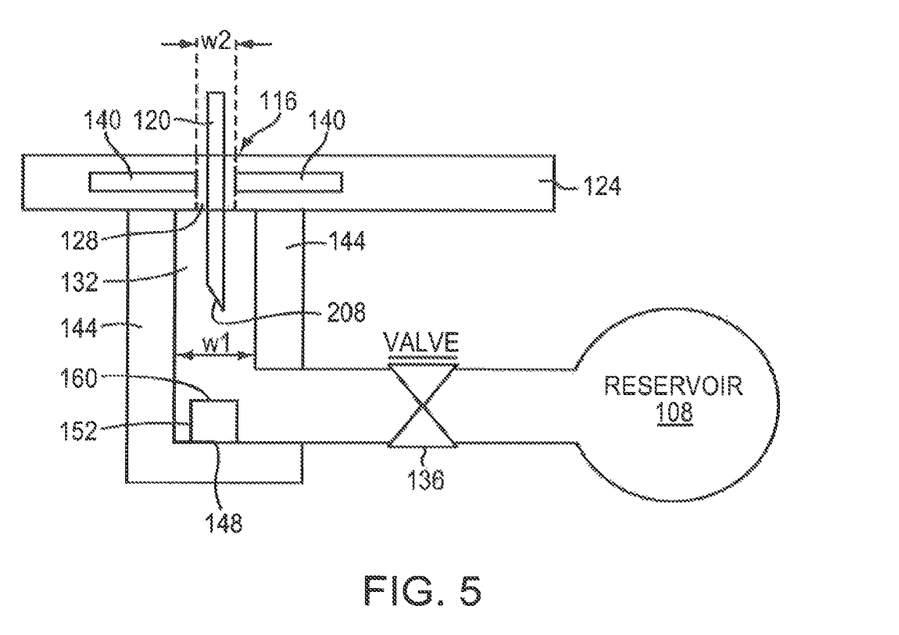
FIG. 5 schematically illustrates a refill needle inserted within a portion of a drug-delivery device, having a stop fixedly mounted to one wall of a vestibule, in accordance with one embodiment of the invention.

In another embodiment, rather than fixedly mounting a stop 224 on the outside of the shaft 212 of the refill needle 120, or in addition thereto, a stop may be positioned within the vestibule 132 of the drug-delivery device 100 itself. For example, as illustrated in FIG. 5, a stop 152 may be secured to, and caused to extend from, the bottom wall 148 of the vestibule 132 (i.e., a wall of the vestibule 132 opposite the throat 128), for example by gluing the stop 152 to the wall 148. In this way, the progress of the refill needle 120 into the vestibule 132 through the throat 128 halts when the tip 208 of the needle 120 contacts the stop 152. Again, in this embodiment, the stop 152 may be sized (i.e., in height), and the fluid exit port(s) 220 placed on the shaft 212 of the refill needle 120, so that the progress of the needle 120 into the vestibule 132 is halted at a point at which the exit port(s) 220 is/are in fluid communication with the vestibule 132.

The stop 152 may be a rectangular prism, a cylinder, or any other shape suitable for carrying out the functions of the stop 152 described herein. As illustrated in FIG. 5, a top surface 160 of the stop 152 may be flat. Alternatively, the stop 152 may be shaped as a cup (e.g., the top surface 160 of the stop 152 may be cup-shaped or concave). In this way, the stop 152 may also aid in preventing the refill needle 120 from contacting, and possibly penetrating, the sidewall 144 of the vestibule 132.

In addition, like the stop 224 of the refill needle 120, the stop 152 may be constructed of a metal, a hard (e.g., fully cross-linked or reinforced) plastic, a composite material, or a combination thereof. For example, the stop 152 may be constructed from a thick layer of PDMS (i.e., a thicker layer than that used for the puncturable surface 124 of the needle entry port 116), polyimide, polypropylene, PEEK, polycarbonate, acetyl film (e.g., acetyl copolymer), polyoxymethylene plastic (e.g., Delrin®), gold, stainless steel, nickel, and/or chrome. The stop 152 may be biocompatible, or not. In general, the stop 152 may be constructed of any relatively rigid and mechanically robust material, or combinations of materials, that have the requisite mechanical strength for performing the functions of the stop 152 described herein.

Figure 6:
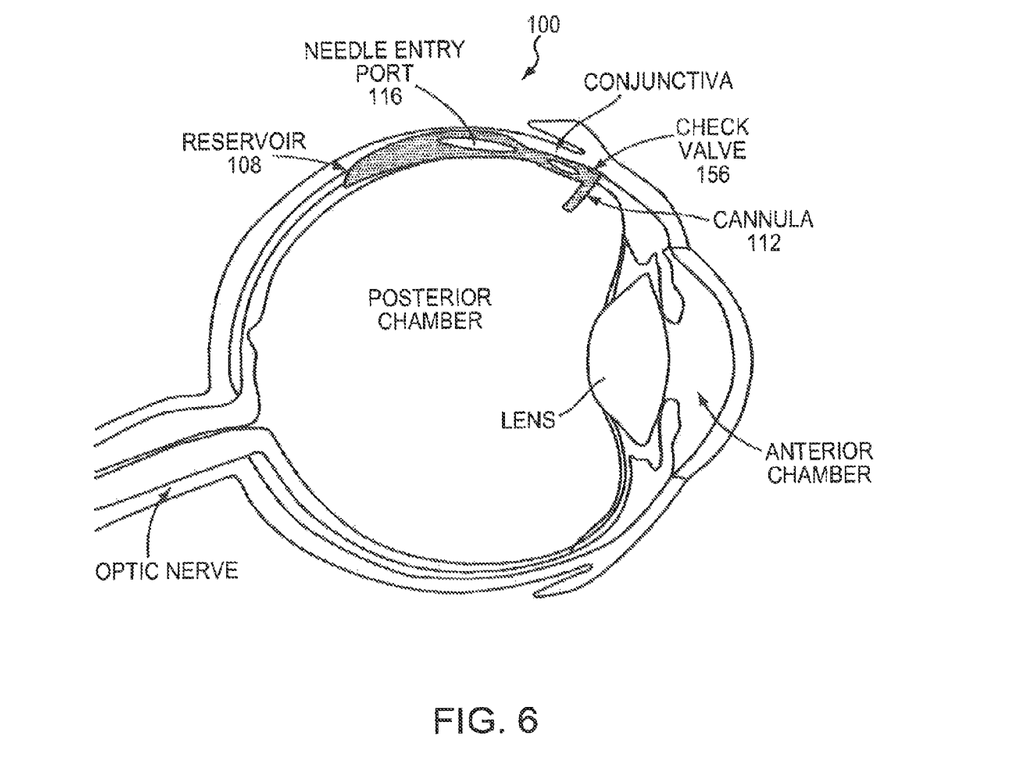
FIG. 6 is a sectional view of a patient's eye illustrating implantation therein of a drug-delivery device in accordance with one embodiment of the invention.

FIG. 6 schematically illustrates the exemplary drug-delivery device 100 implanted in the eye of a patient in accordance with one embodiment of the invention. As illustrated, the device 100 is placed upon the conjunctiva of the eye, and the cannula 112 is inserted therethrough in to the posterior chamber of the eye. The drug-delivery device 100 administers therapeutic fluid to the posterior chamber of the eye through the cannula 112 and a check valve 156, which may control the delivery of the fluid and prevent backflow. In other embodiments, the device 100 is used to administer fluid to the anterior chamber of the eye, which is separated from the posterior chamber by the lens.

An operator of the drug-delivery device 100 (e.g., a physician) may refill the device 100 in situ (i.e., without having to remove the device 100 from the patient's eye). To do so, in one embodiment, the operator first locates the visualization ring 140 of the device 100. The operator may locate the visualization ring 140 by simple visual inspection because, as described above, the visualization ring 140 is constructed of a material that is visible through the patient's conjunctiva. Moreover, because the visualization ring 140 surrounds the needle entry port 116, it visually indicates the position of that needle entry port 116 to the operator.

Once the visualization ring 140 and needle entry port 116 are located, the operator inserts the distal tip 208 of the refill needle 120 into the needle entry port 116 of the drug-delivery device 100. More specifically, the operator may contact the surface 124 of the needle entry port 116 with the distal tip 208 of the refill needle 120, pierce the surface 124 by advancing the needle 120, and further advance the needle 120 into the throat 128 and then the vestibule 132 of the drug-delivery device 100. In an embodiment where the refill needle 120 includes the stop 224 fixedly mounted to (or integral with) its shaft 212, the operator may continue to advance the needle 120 into the needle entry port 116 until the stop 224 contacts the surface 124 of the needle entry port 116, thereby limiting further entry of the needle 120 into the needle entry port 116. Alternatively, in an embodiment where the vestibule 132 includes the stop 152 fixedly mounted to its bottom wall 148, the operator may continue to advance the refill needle 120 into the needle entry port 116 until the distal tip 208 of the needle 120 contacts the stop 152, which then halts further entry of the needle 120 into the vestibule 132.

At the point of the stop 224 and/or the stop 152 acting to limit further entry of the needle 120 into the vestibule 132, the operator will be assured, as described above, that the exit port(s) 220 of the refill needle 120 is/are properly placed within the vestibule 132 and in fluid communication therewith. The operator may then cause a therapeutic fluid (e.g., a drug in liquid form) to be delivered through the hollow shaft 212 of the refill needle 120, out the fluid exit port(s) 220, and into the vestibule 132 of the drug-delivery device 100. Injection of the therapeutic fluid from the needle 120 into the vestibule 132 forces the fluid through the check valve 136 and into the reservoir 108, thereby refilling the reservoir 108.

Accordingly, as described herein, the operator may rapidly refill the drug-delivery device 100 in situ, while the risk of damage to the device 100 and injury to the patient are also minimized.

Having described certain embodiments of the invention, it will be apparent to those of ordinary skill in the art that other embodiments incorporating the concepts disclosed herein may be used without departing from the spirit and scope of the invention. For example, the drug-delivery device 100 may also be implanted in other portions of a patient's body, such as in the sub-arachnoid space of the brain to provide chemotherapy or to provide another type of treatment for the brain, near a tumor in any portion of the patient's body to provide chemotherapy, or in a pancreas that does not respond well to glucose to provide agents (e.g., proteins, viral vectors, etc.) that will trigger insulin release. Accordingly, the described embodiments are to be considered in all respects as only illustrative and not restrictive.

What is claimed is:

1. An implantable drug-delivery device, comprising:
   a drug reservoir;
   a needle entry port comprising a throat for receiving a refill needle therethrough, the throat opening into a vestibule that is in fluid communication with the drug reservoir; and
   a visualization ring surrounding the needle entry port, the visualization ring being visible through ocular tissue so as to visually indicate a position of the needle entry port,
   wherein the vestibule (i) is wider than the throat, and (ii) comprises a stop on a wall opposite the throat for halting progress of a needle into the vestibule through the throat.

2. The implantable drug-delivery device of claim 1, wherein the stop is sized so as to halt the progress of a needle comprising an exit port at a point at which the exit port is in fluid communication with the vestibule.

3. The implantable drug-delivery device of claim 1, wherein a top surface of the stop is cupshaped.

4. The implantable drug-delivery device of claim 1, wherein the stop is constructed of a biocompatible material.

5. The implantable drug-delivery device of claim 1, wherein the stop is constructed of at least one of a metal, a plastic, or a composite material.

6. The implantable drug-delivery device of claim 1, wherein the stop is constructed of a material selected from the group consisting of PDMS, polyimide, polypropylene, PEEK, polycarbonate, an acetyl film, polyoxymethylene plastic, gold, stainless steel, nickel, and chrome.

7. The implantable drug-delivery device of claim 1 further comprising a check valve located between the vestibule and the drug reservoir.

8. The implantable drug-delivery device of claim 1, wherein the needle entry port further comprises a self-sealing material.

9. The implantable drug-delivery device of claim 1, wherein the visualization ring is constructed of a biocompatible material.

10. The implantable drug-delivery device of claim 1, wherein the visualization ring is constructed of a material that withstands penetration by the refill needle.

11. The implantable drug-delivery device of claim 1, wherein the visualization ring is visible through a patient's conjunctiva.

12. The implantable drug-delivery device of claim 1, wherein the visualization ring comprises a light emitting diode.

13. The implantable drug-delivery device of claim 1 further comprising a light emitting diode and optical fiber for conducting light from the light emitting diode to and around the visualization ring.

14. The implantable drug-delivery device of claim 1, wherein the visualization ring comprises a material that enhances surface echogenicity and acoustic shadowing.

15. The implantable drug-delivery device of claim 1 further comprising electronics to move or vibrate the visualization ring.

16. The implantable drug-delivery device of claim 1, wherein the visualization ring comprises a magnetic material.

17. The implantable drug-delivery device of claim 1, wherein the visualization ring comprises a fluorescent pigment.

18. The implantable drug-delivery device of claim 17, wherein the fluorescent pigment is selected from the group consisting of a luminescent aerogel, a nanoparticle, a phthalocyanine pigment, fluorescein isothiocyanate, rhodamine, coumarin, cyanine, an Alexa Fluor, a DyLight Fluor, a quantum dot, a green fluorescent protein, and a luciferin.

* * * * *